United States Patent

Seitz et al.

[11] Patent Number: 5,873,870
[45] Date of Patent: Feb. 23, 1999

[54] FIT AND SUSTAINED FIT OF A DIAPER VIA CHASSIS AND CORE MODIFICATIONS

[75] Inventors: Bret Darren Seitz, West Chester; Gary Dean LaVon, Middletown, both of Ohio

[73] Assignee: The Procter & Gamble Company, Cincinnati, Ohio

[21] Appl. No.: 795,955

[22] Filed: Feb. 5, 1997

Related U.S. Application Data

[63] Continuation of Ser. No. 362,641, Dec. 22, 1994, abandoned.

[51] Int. Cl.⁶ .......................................... A61F 13/15
[52] U.S. Cl. ............................................. 604/385.1
[58] Field of Search ................................ 604/385.1, 385.2

[56] References Cited

U.S. PATENT DOCUMENTS

| | | |
|---|---|---|
| 3,860,003 | 1/1975 | Buell . |
| 3,911,173 | 10/1975 | Sprague, Jr. . |
| 4,336,803 | 6/1982 | Repke .................. 604/385.2 |
| 4,352,355 | 10/1982 | Mesek et al. . |
| 4,573,986 | 3/1986 | Minetola et al. . |
| 4,610,678 | 9/1986 | Weisman et al. . |
| 4,654,246 | 3/1987 | Provost et al. . |
| 4,673,402 | 6/1987 | Weisman et al. . |
| 4,680,030 | 7/1987 | Coates et al. . |
| 4,695,278 | 9/1987 | Lawson . |
| 4,699,622 | 10/1987 | Toussant et al. . |
| 4,704,114 | 11/1987 | Wilson ................. 604/385.2 |
| 4,704,115 | 11/1987 | Buell . |
| 4,785,996 | 11/1988 | Ziecker et al. . |
| 4,834,735 | 5/1989 | Alemany et al. . |
| 4,842,666 | 6/1989 | Werenicz . |
| 4,846,825 | 7/1989 | Enloe et al. . |
| 4,848,572 | 7/1989 | Herrera . |
| 4,850,992 | 7/1989 | Amaral ................. 604/385.1 |
| 4,888,231 | 12/1989 | Angstadt . |
| 4,904,249 | 2/1990 | Miller .................. 604/385.1 |
| 4,909,803 | 3/1990 | Aziz et al. . |
| 4,911,702 | 3/1990 | O'Leary ................ 604/385.2 |
| 4,984,339 | 1/1991 | Provost et al. . |
| 5,021,051 | 6/1991 | Hiuke ................... 604/385.2 |
| 5,032,120 | 7/1991 | Freeland et al. . |
| 5,058,247 | 10/1991 | Thomas et al. . |
| 5,098,423 | 3/1992 | Pieniak ................. 604/385.2 |
| 5,116,563 | 5/1992 | Thomas et al. . |
| 5,147,345 | 9/1992 | Young et al. . |
| 5,151,092 | 9/1992 | Buell et al. . |
| 5,260,345 | 11/1993 | DesMarais et al. . |
| 5,268,224 | 12/1993 | DesMarais et al. . |
| 5,318,445 | 6/1994 | Meier et al. . |
| 5,318,741 | 6/1994 | Thomas . |
| 5,331,015 | 7/1994 | DesMarais et al. . |
| 5,334,152 | 8/1994 | Nomura ................ 604/385.2 |
| 5,358,500 | 10/1994 | LaVon et al. . |
| 5,439,458 | 8/1995 | Noel .................... 604/385.1 |
| 5,451,217 | 9/1995 | Fujioka ................. 604/385.1 |
| 5,462,539 | 10/1995 | Herman ................. 604/385.1 |
| 5,601,547 | 2/1997 | Kato et al. ............. 604/385.2 |

FOREIGN PATENT DOCUMENTS

| | | |
|---|---|---|
| 0 421 473 A3 | 4/1991 | European Pat. Off. . |
| 0 496 567 A3 | 7/1992 | European Pat. Off. . |
| WO 94/09737 | 5/1994 | WIPO . |
| 95/12376 | 5/1995 | WIPO . |

*Primary Examiner*—Michael J. Milano
*Attorney, Agent, or Firm*—William Scott Andes; E. Kelly Linman; J. C. Rasser

[57] ABSTRACT

Absorbent articles such as diapers, incontinent briefs, training pants, diaper holders and liners, feminine hygiene garments, and the like designed to provide sustained dynamic fit about the wearer during use as well as to improve the containment of body exudates and wearer comfort/mobility. Such an absorbent article has an absorbent core preferably designed to fit within the low motion zone of the wearer so that dynamic forces imparted by movements of the wearer on the absorbent core are minimized. the absorbent article is also provided with a closure system for anchoring the absorbent article on the wearer to sustain the dynamic fit of the absorbent article throughout wearing. The closure system is designed so that a plane of tension is formed at least about the front waist portion of the article to preclude rollover of the front waist portion. the absorbent article also features a terraced core including multiple layers of absorbent material, thus allowing exudates to be absorbed at both the top layer and along the exposed edges of the core. Preferred containment assembly designs are also provided.

20 Claims, 3 Drawing Sheets

Fig-3

FIT AND SUSTAINED FIT OF A DIAPER VIA CHASSIS AND CORE MODIFICATIONS

CROSS-REFERENCE TO RELATED APPLICATION

This application is a continuation of application Ser. No. 08/362,641, filed Dec. 22, 1994, now abandoned.

FIELD OF THE INVENTION

The present invention relates to absorbent articles such as diapers, incontinent briefs, training pants, diaper holders and liners, sanitary hygiene garments, and the like, and more particularly, to stretchable absorbent articles which are capable of deforming in response to forces exerted by the wearer and returning to a first configuration in the absence of such forces, thus providing improved fit and sustained dynamic fit about the wearer.

BACKGROUND OF THE INVENTION

Infants and other incontinent individuals wear absorbent articles such as diapers to absorb and contain urine and other body exudates. Absorbent articles function both to contain the discharged materials and to isolate these materials from the body of the wearer and from the wearer's garments and bed clothing. Disposable absorbent articles having many different basic designs are known in the art. For example, U.S. Patent Re. 26,152, entitled "Disposable Diaper" issued to Duncan et al., on Jan. 31, 1967, describes a disposable diaper which has achieved wide acceptance and commercial success, and U.S. Pat. No. 3,860,003, entitled "Contractable Side Portions for Disposable Diaper," issued to Buell on Jan. 14, 1975, describes an elastic leg cuff disposable diaper which has achieved wide acceptance and commercial success, both patents being hereby incorporated by reference.

Many of the known absorbent articles, however, have a tendency to sag or gap away from and to slide/slip down on the body of the wearer during use. This sagging/gapping and sliding/slipping is caused by the relative motions of the wearer as the wearer breathes, moves and changes position, by the downward forces generated when the absorbent article is loaded with body exudates, and by the deformation of the materials of the absorbent article itself when subjected to such wearer's motions. This sagging/gapping and sliding/slipping of the absorbent article can lead to premature leakage and poor fit of the absorbent article about the wearer.

Conventional disposable diapers are typically designed to fit high on the abdomen of the wearer and down on the thighs such that the diaper fits in the zones of the wearer that are subject to dynamic motion (and thus dynamic forces) during use. These dynamic motions and forces, especially by the abdomen bulging and contracting, tend to deform the materials making up the diaper and tend to push the diaper away from the body. Thus, the diaper tends to sag/gap away from the body. The closure system of the diaper is also typically designed to form a defined dimension of the waist and leg openings and a line of tension (imparts a tensile force along a line) about the wearer to secure the diaper of the wearer. However, this defined waist dimension created by the closure system cannot accommodate the changes in body dimension caused by wearer movement such that the diaper tends to slide/slip down on the wearer when the dimension of the abdomen of the wearer becomes smaller than the defined dimension formed by the closure. Further, when the abdominal dimension becomes larger than the defined dimension formed by the closure system, the diaper tends to move to a different position on the wearer (i.e. to the area of minimum circumference) or the diaper tends to be so tight on the abdomen that the diaper can mark the skin or be uncomfortable to wear. The absorbent core and other stiff nonelastic members of the diaper typically fit in the zones of the abdomen or legs that undergo such dynamic forces that the absorbent core bunches and is pushed downward or inward by the dynamic forces resulting in further gapping/sliding of the product on the wearer.

In order to more snugly fit absorbent articles about the wearer, certain commercially available absorbent articles have been provided with elastic features about the waist, hips, or legs. An example of a disposable diaper with an elastic waist feature which has achieved wide acceptance and commercial success is disclosed in U.S. Pat. No. 4,515,595 which issued to Kievit et al., on May 7, 1985, and is incorporated by reference. An example of a disposable diaper with an elastic leg cuff is disclosed in the previously mentioned U.S. Pat. No. 3,860,003. A further example of a disposable diaper with elastic side panels that fit over the hips of the wearer is disclosed in U.S. Pat. No. 4,857,067 which issued to Wood et al., on Aug. 15, 1989, which is also incorporated by reference. The elastic features are designed to expand and contract with the wearer's motions and to maintain the fit of the absorbent article about the wearer during use (i.e., provide sustained dynamic fit). However, it has been found that absorbent articles having elastic features also have a tendency to sag/gap and slide/slip during use.

In addition to addressing problems with the fit and sustained fit of absorbent articles, much attention has been focused on improving the absorbent core structures that function to absorb exudates discharged from the body of the wearer. Commonly, these cores include a conventional absorbent gelling material (referred to herein as an "AGM" material) or a conventional superabsorbent material dispersed in a batt of cellulose fibers. While such core structures typically exhibit good absorbency characteristics, they tend to be limited in their ability to return substantially to their original configuration after being deformed under normal wear situations.

Recent developments in the absorbent article industry have included improved stretchable articles. However, the ability to fully utilize suitable articles is often limited by the lack of integrity and shape retention offered by existing core elements. Thus to improve the overall usefulness of these absorbent articles made with the improved stretchable features, there has arisen a need for core elements which are not greatly limited by a failure to allow for movement of the wearer.

A stretchable absorbent article, namely a sanitary napkin, is disclosed in co-pending commonly assigned PCT application No. W 93/01785, entitled "Stretchable Absorbent Articles." An absorbent elastomeric wound dressing is disclosed in U.S. Pat. No. 4,957,795 (Riedel).

Additional background literature that may be of interest include U.S. Pat. Nos. 3,856,013 (Dulle); 4,229,548 (Sattlegger et al.); 4,341,214 (Fries et al.); 4,554,297 (Dabi); 4,584,324 (Bauman et al.); 3,916,900 (Breyer et al.); 4,394,930 (Korpman); 4,664,662 (Webster); 5,149,720 (DesMarais et al); 4,834,735 (Alemany); 4,610,678 (Weisman et al); 4,673,402 (Weisman et al.); U.S. patent application Ser. No. 08/085,537; entitled "Elastomeric Adhesive Foam;" filed Jun. 30, 1993 in the names of Litchholt and Lodge; and U.S. patent application Ser. No. 08/085,237; entitled "Method of Making an Elastomeric Adhesive Foam and of Elasticizing Garments;" filed Jun. 30, 1993 in the names of Litchholt and Lodge, all of which are incorporated herein by reference.

Attention has thus continued to be focused on developing flexible highly absorbent cores which are useful in association with stretchable articles. For example, U.S. Pat. No. 5,268,224, which issued Dec. 7, 1993, to DesMarais, et al., entitled "Absorbent Foam Materials for Aqueous Body Fluids and Absorbent Articles Containing Such Materials" which is incorporated by reference herein, relates to absorbent foam materials suitable for use as or in the absorbent cores of absorbent articles. Such foamed materials typically comprise hydrophilic, flexible open-celled structures which are preferably prepared by polymerizing high internal phase water-in-oil emulsions having pore volumes of from about 12 to 100 ml/g, and a capillary action specific surface area of from about 0.5 to 5.0 $m^2/g$.

With the advent of more flexible, highly absorbent cores and core materials, attention has turned to utilizing such materials in the most efficient and effective manner possible. Thus, it would be advantageous to provide an absorbent article that provides better fit, reduced leakage, and wearer comfort. It would further be advantageous to provide an absorbent article which has reduced sagging and gapping as well as reduced overall sliding/slipping of the absorbent article and/or the absorbent core on the wearer during use.

It is therefore a primary object of the present invention to provide absorbent articles having improved dynamic fit and sustained fit by utilizing uniquely shaped absorbent cores made from a resilient absorbent material in association with a uniquely designed chassis.

It is a further object of the present invention to provide an absorbent article providing increased comfort for the wearer by providing freedom of motion for the wearer and minimizing the effects of forces caused by wearer's movements on the product's stability.

It is also an object of the present invention to provide an absorbent article including a specifically shaped absorbent core designed to fit within the low motion zone of the wearer, therefore, minimizing the effects of wearer movement on the overall fit of the article.

It is a further object of the present invention to anchor the absorbent article about the perimeter of the low motion zone (otherwise referred to herein as the area of minimum circumference) to achieve sustained dynamic fit.

It is also an object of the present invention to provide a closure system and containment assembly (chassis) design that anchors the absorbent core in the low motion zone of the wearer to enhance the sustained dynamic fit.

It is a further object of the present invention to provide a containment assembly (chassis) design, closure system and an absorbent core shape cooperating to reduce sagging and gapping as well as overall sliding/slipping of the absorbent article during use.

Yet, another object of the present invention is to improve the geometric location of the fastening tabs and the diaper fastening system to enhance the sustained fit of the absorbent article.

Still another object of the present invention is to provide a containment assembly (chassis) design which results in the absorbent article having improved aesthetic characteristics.

These and other advantages of the present invention will be more readily apparent when considered in reference to the following description and when taken in conjunction with the accompanying drawings.

SUMMARY OF THE INVENTION

The present invention provides absorbent articles such as diapers, incontinent briefs, training pants, feminine hygiene garments, and the like, having improved fit and sustained dynamic fit about the wearer during use, as well as providing improved containment of body exudates and wearer comfort. Such an absorbent article has a containment assembly (chassis) comprising a covering layer typically comprising a liquid previous topsheet, a liquid impervious backsheet or outer cover and an absorbent core. The absorbent core is preferably designed to fit along the "low motion zone" of the wearer so that dynamic forces imparted by movements of the wearer on the absorbent core are minimized. For purposes of this invention, the "low motion zone" is defined as the region of the wearer's surface which is not subject to changing shape substantially between standing and sitting positions as will be described in greater detail below.

More specifically, the absorbent core is preferably specifically shaped and made from a resilient, relatively high integrity material such as a foamed absorbent material (FAM). The absorbent article is also provided with a closure system for anchoring the absorbent article on the wearer to sustain the dynamic fit of the absorbent article about the wearer throughout the wearing period. The closure system is designed so that a plane of tension is formed to secure the absorbent article on the wearer in a manner that does not contribute to sagging and/or sliding of the diaper and which precludes the front waist from rolling over. The absorbent article preferably further comprises elastic features for fitting about the extremities of the wearer including a stretch front waist panel, and angled or curved leg elastics and leg cuffs that allow freedom of movement for the wearer as well as maintenance of forces about the body to sustain the fit of the absorbent article.

In a preferred embodiment of the present invention, the absorbent core is designed to fit primarily within the low motion zone of the wearer (i.e., an anatomically low motion zone-fitting absorbent core). By designing the shape of the absorbent core to fit in the low motion zone of the wearer, the absorbent core is not likely to sag/gap or slip/slide during use since the absorbent core is positioned in the area of the wearer having little or no dynamic motions or forces tending to cause such gapping or slippage. The absorbent article is provided with a front waist panel preferably having an arcuate convex shape along the distal edge to fit below or at the abdominal crease of the wearer. It is preferred that the curve of the front waist edge approximate the curve of the abdominal crease of the wearer such that the absorbent core will naturally fit into the low motion zone to maximize the comfort for the wearer. The absorbent article (i.e. the backing sheet, top sheet and absorbent core) is also provided with streamlined, substantially parallel side edges extending rearwardly from the front waist edge designed to fit in the leg creases of the wearer and to define a narrow crotch width which fits between the legs of the wearer. These streamlined side edges of the absorbent core are positioned forward in the absorbent article and extend just beyond the lateral centerline so that the front portion of the absorbent core is shorter in length at the front to fit below the abdominal crease and longer in the rear to allow the absorbent core to fit high over the buttocks, into the lumbar curve of the back. Preferably, the absorbent core is long enough in the back to fit upwardly over the buttocks of the wearer and into the lumbar curve of the back to anchor the back and to provide less gapping of the absorbent core in the back, therefore, further enhancing exudates containment. Ideally, the back portion of the absorbent core will taper downwardly from the rear toward the front where it integrally extends from the crotch width portion to assist in providing sustained fit. Since the absorbent core is preferably formed from a resilient, relatively high integrity material with good fluid transport characteristics, the material utilized eliminates to a great extent the need for greater amounts of capacity in specific areas of the crotch. As a result, the absorbent core can be provided with an overall shape, such as the overall inverted flask shape of the present invention, having a majority of the core's capacity in the rear of the article, which has the least negative impact on the fit and sustained fit of the absorbent article. This benefit is a direct result of the minimized width and storage capacity of the crotch portion of the article.

The absorbent article is also preferably provided with a closure system for anchoring the absorbent article on the wearer. Preferably, the closure system provides both a line of tension around the wearer that fits around the minimum circumference of the wearer to enhance the dynamic fit and to anchor the absorbent core in place so that it will not slip/slide during use, and a plane of tension which precludes rollover of the front waist panel. The line of tension is accomplished through the use of angled tapes disposed along the lower corners of the ears provided on the back portion of the waist panel and an angled landing portion disposed along the outer surface of backing sheet well below the waist line of the wearer.

The plane of tension is accomplished by disposing stiffness beams in the form of strips of mechanical fasteners attached along the back portion of the waist panel which preferably are disposed substantially parallel to the longitudinal center line of the absorbent article. The plane of tension also is established through the use of a stretch laminate front waist panel which is curved along the forward edge to give a straight line upon attachment and a chevroned trailing edge, both of which are positioned outside of the absorbent core to enhance the dynamic fit of the absorbent article about the wearer in those zones that undergo dynamic changes caused by the wearer's movements. Also, contributing to the establishment of a plane of tension are the stretch laminate side closure panels.

BRIEF DESCRIPTION OF THE DRAWINGS

While the specification concludes with claims particularly pointing out and distinctly claiming the subject matter which is regarded as forming the present invention, it is believed that the invention will be better understood from the following description, taken in conjunction with the accompanying drawings wherein like reference materials are used for substantially identical elements, and in which:

DETAILED DESCRIPTION OF THE PREFERRED EMBODIMENT

In general, the present invention is directed to disposable absorbent articles having improved fit upon initial attachment and an enhanced sustained fit after being worn by the individual. More specifically, the present invention relates to the use of a specifically shaped absorbent core and a specifically shaped chassis to form the disposable absorbent article of the present invention. As used herein, the term "disposable absorbent article" refers to products which absorb and contain body exudates and, more specifically, refers to products which are placed against or in proximity to the body of the wearer to absorb and contain the various exudates which are discharged from the body (e.g., urine, feces) and which products are intended to be discarded after a single use (i.e., they are not intended to be laundered or otherwise restored or reused).

A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, herein after diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, training pants, feminine hygiene garments, and the like.

Figures 1, 4A, 4B:
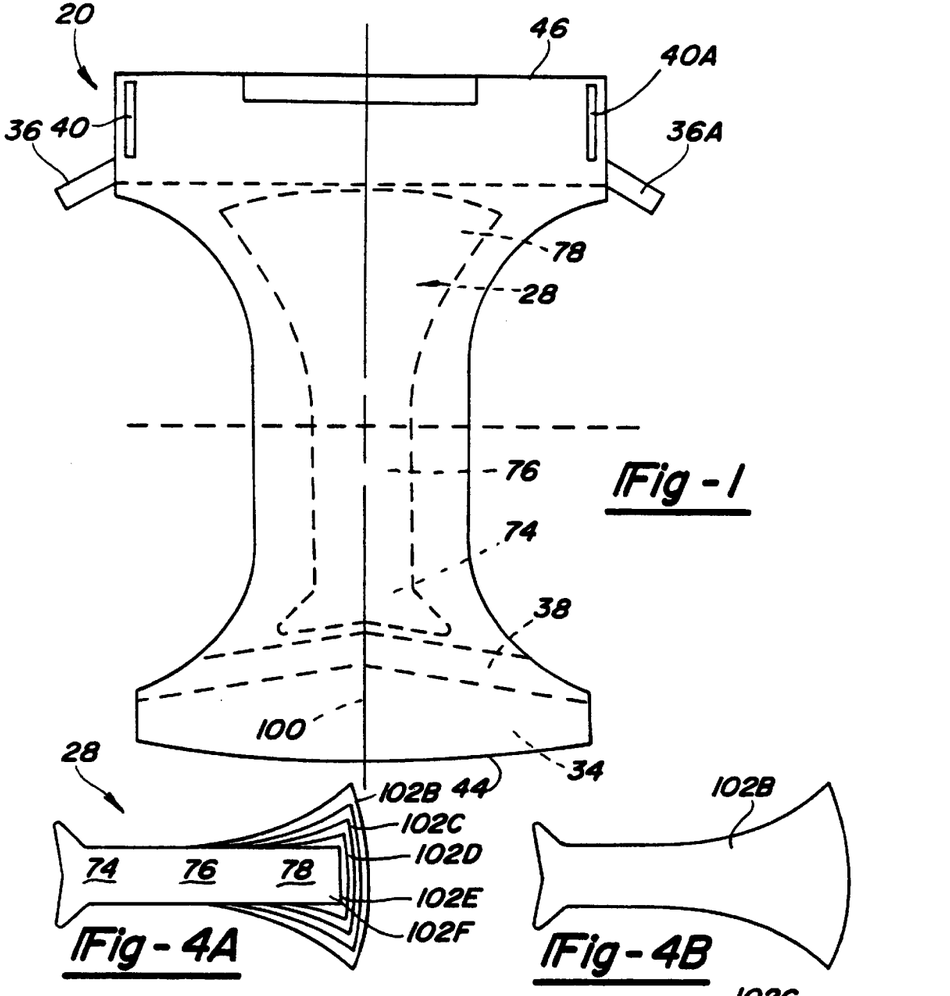
FIG. 1 is a top plan view of an exemplary disposable absorbent article, wherein the inner surface of the diaper faces the viewer.
FIG. 4A is a simplified plan view of the disposable absorbent article embodiment shown in FIG. 1 showing a preferred embodiment of the absorbent core.
FIGS. 4B–4F illustrate the various layers included in the terraced absorbent core embodiment of FIG. 4A.
Figures 2, 5, 6, 7:
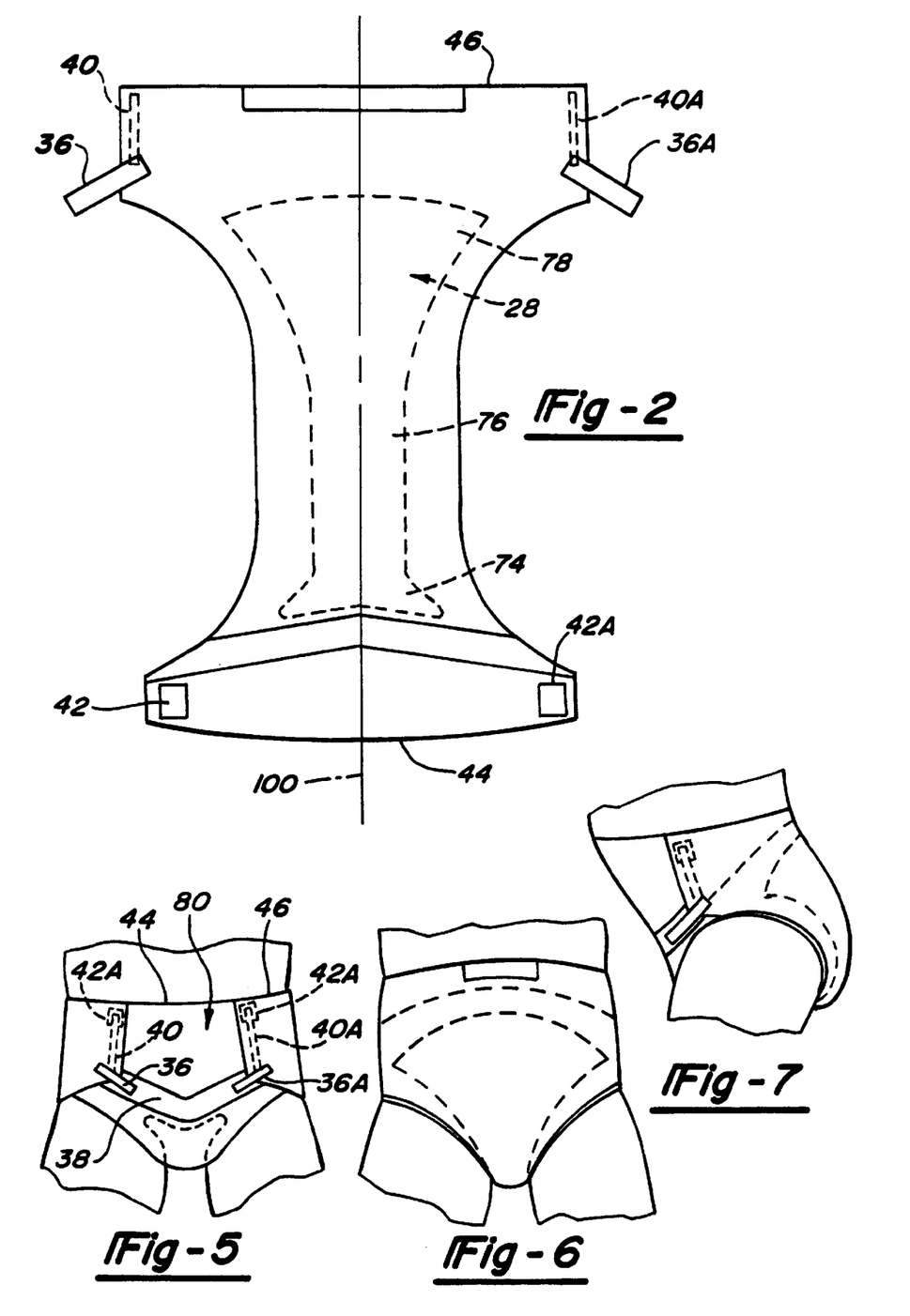
FIG. 2 is a top plan view of an exemplary disposable absorbent article, wherein the outer surface of the diaper faces the viewer.
FIG. 5 is a front coronal view of the body of a wearer showing certain anatomical features and the low motion zone.
FIG. 6 is a back coronal view of the body of a wearer showing certain anatomical features and the low motion zone.
FIG. 7 is a side view of the body of a wearer showing the absorbent article fastened about the minimum circumference of the wearer.
Figure 3:
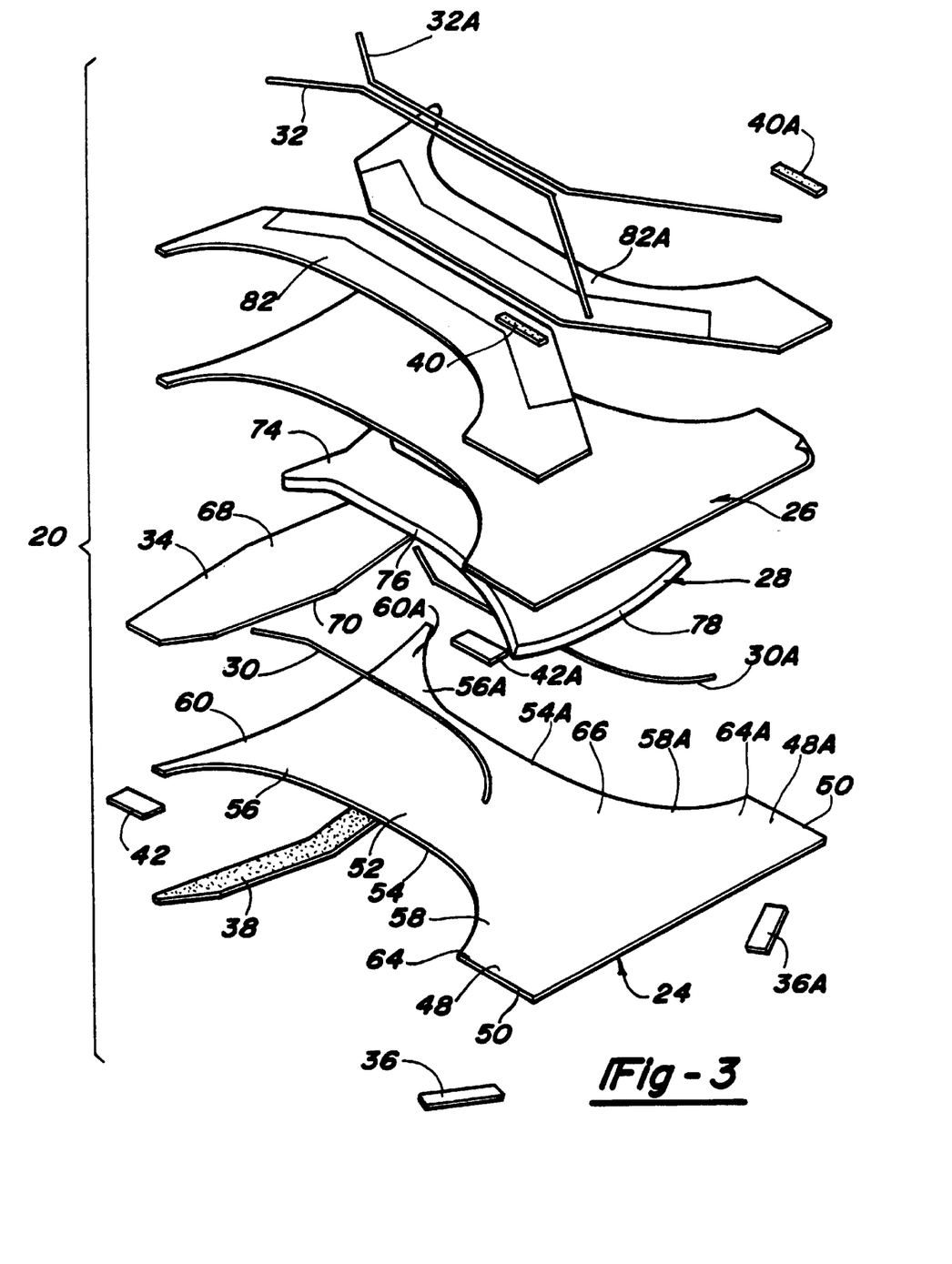
FIG. 3 is a blown apart perspective view of an absorbent article of the present invention including the inverted flask shaped absorbent core.
Figure 4C:
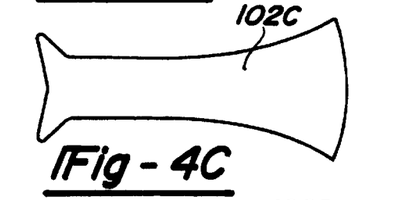
Figure 4D:
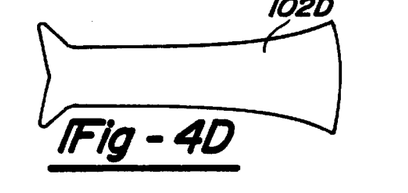
Figure 4E:
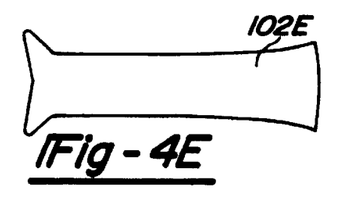
Figure 4F:
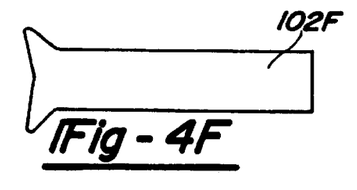

With particular reference to FIGS. 1, 2 and more particularly FIG. 3, a disposable absorbent article, diaper 20, is shown to include a liquid impervious outer backing sheet 24, a liquid permeable topsheet 26 and an absorbent body or core 28 preferably positioned between the backing sheet 24 and the topsheet 26. The topsheet 26 and backing sheet 24 extend beyond the edges of the absorbent core 28 to thereby form the periphery of the containment assembly 22. The diaper 20 also includes leg elastics 30 and 30A and elastic leg cuffs 32 and 32A, a stretch front waist panel 34, and a closure system including a dual tension fastening system. The dual tension fastening system preferably comprises a primary fastening system including a pair of angled tape tabs 36 and 36A which are connected to a fastener landing surface 38 upon closure of the absorbent article about the wearer and a waist closure system preferably comprising fastening members 40 and 40A, which mate with complimentary fastener landing surfaces designated by reference numerals 42 and 42A, respectively.

The backing sheet 24 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backing sheet prevents the exudates absorbed and contained in the absorbent core from wetting articles which contact the diaper such as bedsheets and undergarments. The backing sheet may thus comprise a woven or nonwoven material, polymeric films such as thermoplastic films of polyethylene or polypropylene, or composite materials such as a film-coated nonwoven material. Preferably, the backing sheet is a thermoplastic film having a thickness of from about 0.012 mm (0.5 mils) to about 0.051 mm (2.0 mils).

In a preferred embodiment of the present invention, at least a portion of the backing sheet is subjected to mechanical stretching in order to provide both a "zero strain" stretch laminate that forms the elastic side panels and, if desired, to prestrain the portion of the backing sheet coinciding with the elastic waist feature or any other elastic feature. Thus, the backing sheet is preferably elongatable, most preferably drawable, but not necessarily elastomeric, so that the backing sheet will, upon mechanical stretching, be at least to a degree permanently elongated such that it will not fully return to its original undistorted configuration. In preferred embodiments, the backing sheet can be subjected to mechanical stretching without undue rupturing or tearing. Thus, it is preferred that the backing sheet have an ultimate elongation to break of at least about 400% to about 700% in the cross-machine direction as measured using a method consistent with ASTM D-638. Thus, preferred polymeric films for use as the backing sheet contain a high content of linear low density polyethylene. Particularly preferred materials for the backing sheet include blends comprised of about 45–90% linear low density polyethylene and about 10–55% polypropylene. Exemplary films for use as the backing sheet of the present invention are manufactured by Tredegar Industries, Inc. of Terre Haute, Ind. under the designations X-8323, RR8220 blend for certain blown films, and RR5475 blend for certain cast films.

The backing sheet 24 is preferably embossed (typically, to a caliper of about 0.127 mm [5.5 mils]) and/or matte finished to provide a more clothlike appearance. Further, the backing sheet may permit vapors to escape from the absorbent core (i.e., breathable) while still preventing exudates from passing through the backing sheet.

The backing sheet 24 is positioned adjacent the garment surface of the absorbent core 28 and can be joined thereto by attachment means (not shown) which are well known in the art. For example, the backing sheet 24 may be secured to the absorbent core 28 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waist-Containment Garment" which issued to Minetola and Tucker on Mar. 4, 1986, which is hereby incorporated by reference. Exemplary attachment means of an open pattern are illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989, all of which are incorporated by reference. Alternatively, the attachment means may comprise heat bonds, pressure bonds, ultrasonic bonds, dynamic mechanical bonds, or any other suitable attachment means or combinations of these attachment means as are known in the art.

The topsheet 26 is compliant, soft feeling, and non-irritating to the wearer's skin. Further, the topsheet is liquid pervious permitting liquids (e.g., urine) to readily penetrate through its thickness. A suitable topsheet may be manufactured from a wide range of materials, such as porous foams, reticulated foams, apertured plastic films, or woven or nonwoven webs of natural fibers (e.g., wood or cotton fibers), synthetic fibers (e.g., polyester or polypropylene fibers), or a combination of natural and synthetic fibers. Preferably, the topsheet is made of a hydrophobic material to isolate the wearer's skin from liquids contained in the absorbent core that is treated on at least one side with a surfactant to allow liquids to readily penetrate through its thickness.

In a preferred embodiment of the present invention, at least a portion of the topsheet is subjected to mechanical stretching in order to provide a "zero strain" stretch laminate that forms the elastic side panels. Thus, the topsheet is preferably elongatable, most preferably drawable, but not necessarily elastomeric, so that the topsheet will, upon mechanical stretching, be at least to a degree permanently elongated such that it will not fully return to its original configuration. In preferred embodiments, the topsheet can be subjected to mechanical stretching without undue rupturing or tearing of the topsheet. Thus, it is preferred that the topsheet have a low cross-machine direction (lateral direction) yield strength.

The topsheet 26, which as noted is typically permeable by exudates can also be made from a variety of different materials including, in a non-limiting manner, foamed thermoplastic films, apertured plastic films, porus foams, reticulated foams, natural fibers (e.g., wood or cotton fibers), synthetic fibers (e.g., polyester or polypropylene fibers), and combinations of natural and synthetic fibers and formed films. When the top sheet comprises a nonwoven web, the web may be spunbonded, carded, wet laid, melt-blown, hydroentangled, or formed under a combination of the above. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 in). Preferably, the topsheet has a basis weight from about 18 to about 25 g/m$^2$. A suitable topsheet is manufactured by Veratec, Inc., a division of International Paper Company, of Walpole, Mass., under the designation P-8.

The absorbent core 28 may be any absorbent means which is capable of absorbing and retaining liquids such as urine and other certain body exudates. As shown in the drawings, the absorbent core 28 has an overall shape akin to an inverted flask (when viewed from the top) with a cheveroned first end 74, an elongated relatively narrow crotch portion 76 and a substantially triangular shaped second end 78 which gradually increases in width as the core extends into the rear portion of the diaper 20. Preferably, the absorbent core is positioned within the containment assembly such that a majority, more preferably approximately 75%, of the material comprising the absorbent core is disposed along the back portion.

The absorbent core 28 may be manufactured from a wide variety of liquidabsorbent materials commonly used in disposable diapers and other absorbent articles such as comminuted wood pulp which is often referred to in the absorbent article manufacturing industry as airfelt. Examples of other suitable absorbent materials include creped cellulose wadding, melt-blown polymer fibers or mixtures thereof including coform, chemically modified or cross-linked cellulosic fibers, tissue including tissue wraps and tissue laminates, absorbent foams, absorbent sponges, superabsorbent polymers, absorbent gelling materials, or any equivalent material or combination of materials. The configuration and construction of the absorbent core may also be varied (e.g., the absorbent core may have varying caliper zones, hydrophilic gradients, superabsorbent gradients, or lower average density and/or lower average basis weight acquisition zones; or may comprise one or more layers or structures). The total absorbent capacity of the absorbent core should, however, be compatible with the design loading and the intended use of the absorbent article. Further, the size and the absorbent capacity of the absorbent core may be varied to accommodate wearers ranging from infants through adults.

By way of example, absorbent structures for use as absorbent cores 28 which have achieved wide acceptance and commercial success are described in U.S. Pat. No. 4,610,678 entitled, "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; U.S. Pat. No. 4,834,735, entitled "High Density Absorbent Members Having Lower Density and Lower Basis Weight Acquisition Zones" issued to Alemany et al., on May 30, 1989; U.S. Pat. Nos. 5,331,015 which issued to DesMarais et al. on Jul. 14, 1994, U.S. Pat. No. 5,268,224 which issued to DesMarais et al. on Dec. 7, 1993, and 5,260,345 which issued to DesMarais et al. on Nov. 9, 1993, all three commonly entitled "Absorbent Foam Materials For Aqueous Body Fluids And Absorbent Articles Containing Such Materials;" U.S. Pat. Nos. 5,318,445 which issued to Young et al. on Jun. 7, 1994, and 5,147,345 which issued to Young et al. on Sept. 15, 1992, both of which are commonly entitled "High Efficiency Absorbent Articles For Incontinence Management;" and U.S. Pat. No. 5,385,500, entitled "Absorbent Articles Providing Sustained Dynamic Fit" which issued to LaVon et al., on Oct. 25, 1994; each of the above-listed references being hereby expressly incorporated by reference.

When the absorbent core 28 is formed from a foamed polymeric material such as those disclosed in the references set forth in the preceding paragraph, preferably the core is capable of swelling, when saturated with fluid, from 5 to 8 times their original thickness and will typically expand peripherally to a significantly lesser degree than other known materials. Thus, it is important to size the core such that maximum absorption can be accomplished while still precluding the core from expanding into the region of the plane of tension. By limiting expansion of the core 28 from entering the so-called plane of tension, designated by reference numeral 80, the degree of separation of the diaper from the wearer's back can be kept to a minimum.

Under a highly preferred embodiment, the absorbent core 28, will have a terraced construction including multiple layers as illustrated most clearly in FIGS. 4A–4F. By "terraced," it is meant that each successive layer of material, from the layer 102B shown in FIG. 4B disposed closest to the backing sheet 24 to the layer 102F shown in FIG. 4F which is disposed closest to the top sheet 26 becomes wider along a predetermined portion of the absorbent core. Preferably, this difference in the peripheral dimensions of successive layers (i.e. layers 102B–102F in five layer constructions) occurs primarily along the second end 78 of the absorbent core 28. Under certain embodiments, it also may be desirable to provide this so-called "terraced" effect along the first end 74 and possibly the crotch portion 76 of the core as well. While it is preferred that the so-called "terraced" effect be continuous over segments of the cores periphery, it should be understood by those skilled in the art that the terraced effect can be intermittent along the periphery. It should be further recognized that under certain embodiments, each successive layer needs not be wider than both contiguous layers.

To accommodate for the decreased cross-sectional area of the cores 28 of the present invention, the overall thickness of the core 28 is enhanced to allow for substantially the same absorption capacity as that offered by full-sized cores. The total wet thickness of the core will, therefore, typically range from between about 0.5 inches to about 0.75 inches for the cores 28 offered in accordance with the teachings of the present invention. With regard to the so-called "terraced" cores of the present invention, it is important to note that while the total absorption capacity is substantially equal to conventional full-sized cores, the overall performance is believed to be enhanced over non-terraced conventional cores in that fluids can enter the core layers from both the exposed sides and the top instead of just the top as is typically the case with conventional core structures.

With further reference to FIG. 3, each of the components which contribute to the overall construction of the diaper 20 will now be described in greater detail. The backing sheet 24 which has an overall modified hour glass design preferably includes a first end 44 shown to have a substantially chevroned shape and an enlarged, somewhat rectangular shaped second end 46 having ear portions 48 and 48A disposed proximate to the diametrically opposed longitudinally extending edges 50 and 50A, respectively. Located between the first and second ends is an elongated, relatively narrow crotch portion 52. The crotch portion 52 is defined by longitudinal extending substantially parallel side edges 54 and 54A, respectively, which are curved outwardly as the crotch portion 52 merges with the first end 44 along each side as designated by reference numerals 56 and 56A, respectively. Likewise, the substantially parallel side edges 54 and 54A also curve outwardly as the crotch portion 52 merges with the second end 46 along each side as designated by reference numerals 58 and 58A, respectively. Under preferred embodiments, the crotch portion 52 has a width of between approximately 4.25 inches to about 5.0 inches which is substantially more narrow than conventional diapers which typically have a crotch width of up to about 8.0 inches.

Attached to the outer surface 60 of the backing sheet 24 along the first end 44 is an angled, somewhat V-shaped fastener landing surface 38 made from materials such as highly shear resistant polyethylene or polypropylene, with or without reinforcing means such as an applied or embedded scrim as disclosed in U.S. Pat. No. 4,699,622 entitled "Disposable Diaper Having An Improved Side Closure" which issued Oct. 13, 1987 to John W. Toussant et al., is hereby incorporated by reference. Regardless of the material used to form the fastener landing surface 38, ideally the material will be highly conducive to the adhesive material contained on tape tabs 36 and 36A.

Disposed on the outer surface of the backing sheet along the forward most corners 64 and 64A of ear portions 48 and 48A are the tape tabs 36 and 36A, respectively, which are both angled outwardly and in the relative direction of the first end 44 such that the tape tabs are disposed at an angle of approximately 45° from the longitudinal edges 50 and 50A. This approximate 45° angle of disposition allows the tape tabs to attach to the fastener landing surface 38 such that the absorbent article can be disposed about the minimum circumference of the wearer. Under preferred embodiments, not only are the tape tabs angled, but they are also more narrow than conventional tape tabs such as those disclosed in U.S. Pat. Nos. 5,358,500 entitled "Absorbent Articles Providing Sustained Dynamic Fit" which issued Oct. 25, 1994, to LaVon et al; which is hereby incorporated by reference.

Due essentially to the unique design of the absorbent article described herein, and more particularly, to the sustained dynamic fit offered by such article, relatively narrow tape tabs can be utilized without compromising the integrity of the closure. Thus, the tape tabs 36 and 36A have an average width of approximately 0.50 inches as opposed to conventional tape tabs which have an average width of 1.0 inches or more.

Also disposed on the outer surface of the backing sheet 24 along the ear portions 48 and 48A are mechanical fasteners 42 and 42A. The fasteners 42 and 42A which are in the form of elongated strips disposed substantially parallel to the longitudinal axis designated by reference numeral 100, can be in a variety of forms including VELCRO® hooks and/or loops, such as those disclosed in U.S. Pat. Nos. 4,654,246 entitled "Self-Engaging Separable Fastener" which issued Mar. 31, 1987, to Provost et al.; and 4,984,339 entitled "Hook For Hook and Loop Fasteners" which issued Jan. 15, 1991, to Provost et al. More preferably, the fasteners 42 and 42A are in the form of Thomas hooks and/or loops, such as those described in U.S. Pat. No. 5,318,741 entitled "Process Of Making A Refastenable Mechanical Fastening System" which issued Jun. 7, 1994, to Dennis A. Thomas; U.S. Pat. No. 5,116,563 entitled "Process for Producing a Mechanical Fastener" which issued May 26, 1992, to Dennis A. Thomas et al.; and U.S. Pat. No. 5,058,247 entitled "Mechanical Fastening Prong" which issued Oct. 22, 1991, to Dennis A Thomas et al., each of the above-listed patents being hereby incorporated by reference. The mechanical fasteners provide resistance to any undesired separation forces which may occur. As will be described in greater detail below, fasteners 42 and 42A assist in providing a so-called "plane of tension" along the front edge of the diaper upon securement about the wearer to preclude rollover of the front of the diaper which is a common problem with many commercially available products.

Attached to the inner surface of the backing sheet 24 along the longitudinal edges 54 and 54A of the crotch portion 52 are outwardly curved leg elastics 30 and 30A. The leg elastics 30 and 30A which may be attached to the backing sheet 24 in a variety of manners, including but not limited to adhesive bonding and ultrasonic welding, allow for improved containment of liquids and exudates adjacent the wearer's leg. Ideally, the leg elastics 30 and 30A will follow the contour of the longitudinal side edge 54 and 54A of the crotch portion and extend into the curved areas 56, 58 and 56A, 58A respectively.

Also provided are a pair of spaced apart elastic leg cuffs 32 and 32A typically disposed between the curved leg elastics 30 and 30A. The elastic leg cuffs 32 and 32A may comprise any one of a number of different embodiments. By way of example, U.S. Pat. No. 3,860,003 entitled "Contractable Side Portions For A Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al., on Mar. 29, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sept. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edgeleakage-guard gutters configured to contain free liquid within the garment. U.S. Pat. No. 5,032,120 entitled "Disposable Absorbent Article Having Improved Leg Cuffs" issued to Freeland et al., on Jul. 16, 1991, discloses a disposable diaper having improved elastic leg cuffs. The above-listed patents are all expressly incorporated herein by reference.

While each elastic leg cuff 32 and 32A may be configured so as to be similar to any of the leg bands, gasketing cuffs, side flaps, barrier cuffs, or elastic cuffs described above, it is preferred that each elastic leg cuff 32 and 32A include an elastomeric leg cuff tackdown member 82 and 82A, respectively. The barrier elastic leg cuffs 32 and 32A may be attached to the tackdown members 82 and 82A by sewing the two components together, adhering them or otherwise attaching them as is known in the art.

In addition to the narrow crotch width of the diaper, which is allowed by the core properties, the curved or angled elastic leg cuffs 32 and 32A provide the additional benefit of delivering both horizontal and vertical components of force (outward from the center of the wearer) which helps maintain contact with the wearer's legs, unlike conventional linear elastic leg cuffs which only offer vertical components of force.

The diaper 20 also includes a stretchable front waist panel 34 having elastomeric properties which is generally disposed along the first end 44. The stretchable front waist panel 34 which can be formed from a variety of different materials, preferably comprises a unitary waistband formed by a single piece of elastomeric material operatively associated with the topsheet 26. The waist panel 34 is typically disposed adjacent the first end of the disposable absorbent article by a waistband securement means (not shown) such as an adhesive or other art disclosed securement means.

Under highly preferred embodiments, the stretchable front waist panel 34 has an outwardly curved leading edge 68 and a chevron-shaped trailing edge 70 which terminates proximate to the area occupied by the fastener landing surface 38.

For a better understanding of suitable materials from which the elastic waist panel of the present invention can be formed, reference can be made to any one of a number of different references, including, but not limited to U.S. Pat. No. 5,151,092, entitled "Absorbent Article With Dynamic Elastic Waist Feature Having A Predisposed Resilient Flexural Hinge," which issued on Sept. 29, 1992, to Buell et al., which is hereby incorporated by reference.

FIGS. 5, 6 and 7 show front coronal, rear coronal and side views, respectively, of a wearer illustrating the location of the low motion zone of the wearer. The low motion zone is delineated by the dot and dash designation in the drawings. As defined by the wearer, the "low motion zone" is defined to mean the zone or area of the body which despite dynamic movements remains substantially undeformed or undergoes very little motion. As shown in FIG. 5, the low motion zone occurs immediately below the arcuate line in the hypogastric abdominal region under the crease or fold created by the rectus abdominus muscle. The abdominal crease is typically the fold or flexton crease of skin or muscle created by the abdomen when the wearer goes into a sitting position. The low motion zone is bounded on each lateral side by an arcuate line connecting the anterior superior iliac spine through the perineum along the inguinal ligament under the gluteus maximus (along the gluteal fold) to about the posterior inferior iliac spine. As shown in FIG. 6, the low motion zone is bounded on the posterior of the wearer by the line connecting the posterior inferior iliac spine over the gluteus maximus and along the lumbar curve of the back (the small of the back). For purposes of the present invention, the low motion zone also includes the zone or area of the gluteus maximus despite the fact that the gluteus maximus undergoes some dynamic motion since the forces generated in this zone caused by the wearer's movements tend to push up the absorbent core over the buttocks into the lumbar curve to enhance the fit of the absorbent core and the diaper rather than degrade such fit.

With the major components of the absorbent article of the present invention being described above, closure of the absorbent article about a wearer will now be described in greater detail. The diaper 20 is preferably applied to the wearer by positioning the back waist region under or against the wearer's back and drawing the remainder of the diaper between the wearer's legs so that the front waist region is positioned across the front of the wearer. The front waist portion is laid adjacent to the lower abdominal area of the wearer and the ear portions 48 and 48A of the back waist region are applied over the sides 60 and 60A of the front waist panel as illustrated in FIG. 5 such that the mechanical fasteners 40 and 40A mate with the corresponding fastener landing surfaces 42 and 42A disposed on the outer surface of the diaper 20 along the sides of 60 and 60A of the front waist panel portion.

Once the initial waist closure has been accomplished, the primary fastening means are employed to assist in maintaining the fit and sustained fit of the diaper about the wearer. As noted, the tape tabs 36 and 36A are disposed at an angle of approximately 45° relative to the longitudinal side edges 50 and 50A of ear portions 48 and 48A. The first tape tab 36 is applied to adhere to the reinforced landing surface 38. Thereafter, the second tape tab 36A is applied to adhere to the reinforced landing surface 38 to fully effectuate closure, thus establishing the plane of tension in association with the fasteners 40 and 40A of the waist closure system across the front waist panel.

As the application of the diaper 20 is carried out from the back waist panel to the front waist panel prior to effectuating a closure of the diaper, the elastic side panels and the back elastic waist feature, if any, will typically be extended in tension during this operation so as to conform to the size and shape of the wearer. According to the preferred embodiment of the present invention, when closure about the wearer's waist is accomplished, the front elastic waist feature is pretensioned so as to provide the snug fit described herein. The absorbent core becomes positioned within the low motion zone of the wearer and the diaper is anchored in its ultimate, sustainable wearing position by the plain of tension accomplished upon closure and fastening of the diaper. As can be seen from a review of FIG. 5, the plain of tension also serves to anchor the absorbent core below the abdominal crease. As previously noted, those portions of the diaper 20 located outside the low motion zone adaptable to fit the changing dimensions of the wearer with the front elastic waist feature intended to prevent rollover, sagging and gapping. Thus, the diaper remains in its initial fit position and does not sag, gap, slide/slip on the wearer during use.

While the particular embodiments of the present invention have been illustrated and described, it should be recognized by those skilled in the art that various other changes and modifications can be made without departing from the spirit scope of the present invention. It is therefore, intended to cover in the dependent claims all such changes and modifications that are within the scope of the present invention.

What is claimed:

1. An absorbent article for fitting about a wearer to contain body exudates, the wearer having a low motion zone, the absorbent article comprising:

a containment assembly having a front waist region, a back waist region opposed to the front waist region, a first end, a second end, longitudinal edges extending between said first end and said second end, and a longitudinal axis, said containment assembly further comprising:
a topsheet;
a backing sheet,
an anatomically low motion zone-fitting absorbent core positioned between said topsheet and said backsheet, said absorbent core having a first end adjacent to said front waist region defining a front relatively narrow portion, a substantially triangular shaped second end adjacent to said back waist region defining an enlarged back portion, and an elongated, relatively narrow crotch portion located between said first end and said second end and defined by longitudinally extending substantially parallel side edges, said back portion having a generally continuously increasing width as the back portion progresses rearwardly from said crotch region to said second end, said absorbent core being positioned within said containment assembly such that a majority of the material comprising the absorbent core is disposed along the back portion; and
closure means for anchoring the absorbent article on the wearer, said closure means including a plane of tension along at least the front waist region of the containment assembly to assist in precluding rollover of said front waist region upon closure of the absorbent article.

2. The absorbent article of claim 1, wherein said containment assembly further comprises a leg closure assembly including a pair of spaced apart leg elastics attached to either said backing sheet or said topsheet, said leg elastics including a first end extending into the front waist portion, a substantially longitudinally extending portion and a second end extending into the back waist portion, wherein at least one of said first or second end portions extend in an arcuate manner outwardly from said longitudinally extending portion.

3. The absorbent article of claim 2, wherein said leg closure assembly further comprises a pair of spaced apart barrier leg cuffs attached to said containment assembly and disposed between said leg elastics, said barrier leg cuffs including a first end extending into the front waist portion, a substantially longitudinally extending portion and a second end extending into the back waist portion, wherein at least one of said first or second end portions extend in an arcuate manner outwardly from said longitudinally extending portion.

4. The absorbent article of claim 1, wherein said closure means further comprise a waist closure assembly, said waist closure assembly comprising:

a pair of spaced apart mechanical fasteners disposed along the back waist region of the containment assembly, said mechanical fasteners being disposed substantially parallel to the longitudinal axis of said containment assembly to form a pair of elongated longitudinally-extending stiffening beams; and complimentary mechanical fastener landing surfaces disposed along the front waist portion of the containment assembly, whereby upon properly attaching the absorbent article to a wearer, the mechanical fasteners engage the mechanical fastener landing surfaces to assist in forming said plane of tension.

5. The absorbent article of claim 4, wherein said closure means further comprise a primary fastening system, said primary fastening system comprising:

a reinforced fastener landing surface disposed on said covering layer below the front waist portion of said containment assembly and fastening tabs extending at a downward angle from said back waist region along spaced apart longitudinally extending edges, whereby upon partially overlapping said back waist region onto said front waist region, said fastening tabs engage said fastener landing surface to effect a sustained closure of the absorbent article.

6. The absorbent article of claim 5, wherein said fastening tabs are adhesive and have an average width of less than 0.5 inches.

7. The absorbent article of claim 5, wherein said fastener tabs extend at a downward angle of approximately 45° relative to the longitudinal side edges of the back waist region.

8. The absorbent article of claim 1, wherein said first end of said absorbent core has a cheveroned shape.

9. The absorbent article of claim 1, wherein said second end of said absorbent core has a width greater than that of said first end of said absorbent core.

10. An absorbent article for fitting about a wearer to contain body exudates, the wearer having a low motion zone, the absorbent article comprising:

a containment assembly having a front waist region, a back waist region opposed to the front waist region, a first end, a second end, longitudinal edges extending between said first end and said second end, and a longitudinal axis, said containment assembly further comprising:
a topsheet;
a backing sheet;
an anatomically low motion zone-fitting absorbent core positioned between said topsheet and said backsheet, said absorbent core having a first end adjacent to said front waist region defining a front relatively narrow portion, a substantially triangular shaped second end adjacent to said back waist region defining an enlarged back portion, and an elongated, relatively narrow crotch portion located between said first end and said second end and defined by longitudinally extending substantially parallel side edges, said back portion having a generally continuously increasing width as the back portion progresses rearwardly from said crotch region to said second end, said absorbent core being positioned within said containment assembly such that a majority of the material comprising the absorbent core is disposed along the back portion, said absorbent core including a plurality of layers, said plurality of layers including a first layer and a second layer, said first layer being located closer to said topsheet than said second layer and having smaller peripheral dimensions along at least a portion thereof than said second layer; and closure means for anchoring the absorbent article on the wearer, said closure means including a plane of tension along at least the front waist region of the containment assembly to assist in precluding rollover of said front waist region upon closure of the absorbent article.

11. The absorbent article of claim 10, wherein additional layers are provided with each successive layer having larger peripheral dimensions along at least a portion thereof than the preceding layers.

12. An absorbent article for fitting about a wearer to contain body exudates, the wearer having a low motion zone, the absorbent article comprising:

a containment assembly having a front waist region, a back waist region opposed to the front waist region, a first end, a second end, longitudinal edges extending between said first end and said second end, a longitudinal axis and a leg closure assembly including leg elastics for accomplishing closure about the wearer's legs, said containment assembly further comprising:
a topsheet, a backing sheet, and an anatomically low motion zone fitting absorbent core positioned between said topsheet and said backsheet, said absorbent core having a first end adjacent to said front waist region defining a relatively narrow front portion, a substantially triangular shaped second end adjacent to said back waist region defining an enlarged back portion, and an elongated, relatively narrow crotch portion located between said first end and said second end and defined by longitudinally extending substantially parallel side edges, said back portion having a generally continuously increasing width as the back portion extends rearwardly from said crotch region to said second end, said absorbent core being positioned within said containment assembly such that approximately 75% of the material comprising the absorbent core is disposed along the back portion; and
closure means for anchoring the absorbent article on the wearer, said closure means including a primary fastening system and a waist closure system, said waist closure system comprising:
a pair of spaced apart mechanical fasteners disposed along the back waist region of the containment assembly on said backing sheet, said mechanical fasteners being disposed substantially parallel to the longitudinal axis of said containment assembly to form a pair of elongated longitudinally-extending stiffening beams; and
complimentary mechanical fastener landing surfaces disposed along the front waist portion of the containment assembly, whereby upon properly attaching the absorbent article to a wearer, the mechanical fasteners engage the mechanical fastener landing surfaces to provide a plane of tension along at least the front waist region of the absorbent article.

13. The absorbent article of claim 12, wherein said leg closure assembly further comprises a pair of spaced apart barrier leg cuffs attached to said containment assembly and disposed between said leg elastics, said barrier leg cuffs including a first end extending into the front waist portion, a substantially longitudinally extending portion and a second end extending into the back waist portion, wherein at least one of said first or second end portions extend in an arcuate manner outwardly from said longitudinally extending portion.

14. The absorbent article of claim 12, wherein said absorbent core includes a plurality of layers.

15. The absorbent article of claim 14, wherein said plurality of layers include a first layer and a second layer having a similar geometry to said first layer, said first layer having smaller peripheral dimensions than said second layer.

16. The absorbent article of claim 15, wherein said closure means further comprise a primary fastening system, said primary fastening system comprising:

a reinforced fastener landing surface disposed on said backing sheet below the front waist portion of said containment assembly and fastening tabs extending at a downward angle from said back waist region along spaced apart longitudinally extending edges, whereby upon partially overlapping said back waist region onto said front waist region, said fastening tabs engage said fastener landing surface to effect a sustained closure of the absorbent article.

17. The absorbent article of claim 16, wherein said fastening tabs adhesively attach to said fastener landing surface.

18. The absorbent article of claim 17, wherein said fastening tabs extend at a downward angle of approximately 45° relative to the longitudinal side edges of the back waist region.

19. The absorbent article of claim 12, wherein said first end of said absorbent core has a cheveroned shape.

20. The absorbent article of claim 12, wherein said second end of said absorbent core has a width greater than that of said first end of said absorbent core.

* * * * *